United States Patent [19]

Alexander

[11] Patent Number: 4,760,057

[45] Date of Patent: Jul. 26, 1988

[54] (ACYLOXYALKOXY)CARBONYL DERIVATIVES AS BIOREVERSIBLE PRODRUG MOIETIES FOR PRIMARY AND SECONDARY AMINE FUNCTIONS IN DRUGS

[75] Inventor: Jose Alexander, Lawrence, Kans.

[73] Assignee: Merck & Co., Inc., Rahway, N.J.

[21] Appl. No.: 725,605

[22] Filed: Apr. 22, 1985

Related U.S. Application Data

[63] Continuation-in-part of Ser. No. 507,316, Jun. 23, 1983, abandoned.

[51] Int. Cl.$^4$ .................. C07C 125/04; A61K 31/495; A61K 31/555; C07D 401/10
[52] U.S. Cl. .................................. 514/187; 514/254; 514/299; 514/306; 514/314; 514/320; 514/330; 514/338; 514/341; 514/342; 514/365; 514/394; 514/396; 514/479; 514/481; 514/484; 514/488; 544/121; 544/135; 544/358; 544/363; 544/365; 546/112; 546/153; 546/156; 546/158; 546/165; 546/167; 546/200; 548/146; 548/181; 548/201; 548/204; 560/19; 560/24; 560/30; 560/31; 560/32; 560/51; 560/161; 560/162; 560/163; 560/167; 560/165; 514/234.5; 514/235.2; 514/235.8; 514/237.5

[58] Field of Search ............... 544/363, 358, 121, 135, 544/358, 363, 365; 560/165; 514/187; 548/146, 181, 201, 204

[56] References Cited

U.S. PATENT DOCUMENTS

| 4,156,784 | 5/1979 | Dockner et al. | 560/165 |
| 4,292,317 | 9/1981 | Pesson | 544/363 |
| 4,522,819 | 6/1985 | Fox, Jr. et al. | 544/363 |
| 4,544,747 | 10/1985 | Ishikawa et al. | 544/363 |

OTHER PUBLICATIONS

L. G. Agood, Journal of Medicinal Chemistry, 13, 1176 (1970).

*Primary Examiner*—Glennon H. Hollrah
*Assistant Examiner*—Raymond Covington
*Attorney, Agent, or Firm*—Manfred Polk; Michael C. Sudol

[57] ABSTRACT

This invention relates to novel (acyloxyalkoxy)carbonyl derivatives as bioreversible prodrug moieties for primary and secondary amine functions in drugs having a primary or secondary amine function thereon. Hydrolytic enzymes are used to trigger the regeneration of the parent amine drug of the carbamate prodrug moiety. The case also contains pharmaceutical composition, method of treatment and process claims.

15 Claims, No Drawings

(ACYLOXYALKOXY)CARBONYL DERIVATIVES AS BIOREVERSIBLE PRODRUG MOIETIES FOR PRIMARY AND SECONDARY AMINE FUNCTIONS IN DRUGS

This is a continuation-in-part application of U.S. Ser. No. 507,316, filed June 23, 1983 now abandoned.

BACKGROUND OF THE INVENTION

Drugs or pharmaceutical and medicinals which are amines or have an amine function therein undergo protonation at physiological pH and are not always transported optimally through biological membranes in the body. No bioreversible chemical modification of the amine-type drugs, or pharmaceutical and medicinals having amine functions thereon to prevent protonation are known. Enamines have been studied in the past, but they depend on acid catalyzed hydrolysis for regeneration, not on an enzymatic process, and thus are unsatisfactory. Also, carbamate ester latentiation of physiologically active amines has been described in A. J. Verbiscar and L. G. Agood, *Journal of Medicinal Chemistry*, 13, 1176 (1970), but these compounds were also not bioreversible.

For the purposes of this specification, the term "prodrug" denotes a derivative of a known and proven primary or secondary amino functional drug (e.g. timolol, methyldopa, thiabendazole, etc.) which derivative, when administered to a warm-blooded animal, "cleaves" in such a manner as to release the proven drug form at its target site or sites of activity. The enzymatic and/or chemical hydrolytic "cleavage" of the compounds of the instant invention occurs in a manner such that the proven drug form is released while the remaining "cleaved" moiety remains nontoxic and is metabolized in such a manner that nontoxic, metabolic products are produced.

SUMMARY OF THE INVENTION

For compounds which ionize the rate of transport through biomembranes appear to be proportional to the concentration of undissociated molecules and the lipid solubility. It is often advantageous to perform derivatization of polar groups to aid absorption, since this would make the compounds more hydrophobic and hence more lipid soluble. Carbamylation confers such properties to amines since carbamates do not ionize. However, success with carbamate ester latentiation requires that it must be hydrolyzed to carbamic acid and the alcohol moiety after penetration through the biological barrier. This is especially true of carbamates of secondary amines, the rates of hydrolysis of which are $10^5$–$10^9$ times slower than that of the corresponding primary amines. In this regard, there does not appear to be a carbamate ester specific hydrolytic enzyme in mammals. Though cholinesterases hydrolyze carbamates and become reversibly inhibited in the process, the rates are too slow for practical use. Hence, modified carbamates with an enzymically hydrolyzable ester function are designed as prodrugs for amines. Esterase catalysed hydrolysis of the ester moiety triggers the regeneration of the parent amine from such derivates as depicted below.

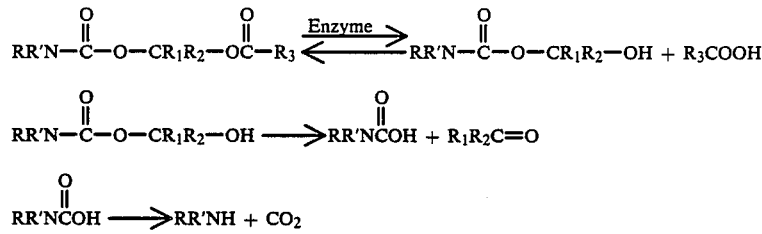

wherein RR'N, $R_1$, $R_2$ and $R_3$ are as defined further along.

Thus, it is an object of this invention to provide (acyloxyalkoxy)carbonyl derivatives as bioreversible prodrug moieties for drugs or medicaments having primary or secondary amine functions thereon which when administered to warm-blooded animals are characterized as being more readily bioavailable, less irritating to topical and gastric mucosal membranes and more permeable through topical membranes, e.g., ophthalmic membrane or skin, than are the parent drugs from which they are derived. Thus, the prodrugs of the amines of the present invention may be used wherever increased biomembrane transport is beneficial such as in improving the bioavailability from the gastrointestinal tract, the rectum, the skin, and the eye. As such, the prodrugs of the instant invention can be incorporated in the usual dosage forms such as tablets, capsules, suspensions, ointments, and the like, depending on the particular drug or medicament and its target area.

It is another object of the present invention to provide such prodrug form of conventional primary and secondary amine compounds which, following administration, will "cleave" in such a manner as to enable the original parent moiety to be released at its therapeutic site or sites of activity and to further permit the cleaved moiety, unassociated with the parent moiety, to be metabolized in a nontoxic fashion.

It is still another object of this invention to provide prodrugs of medicaments or drugs having primary or secondary amine functions thereon to provide increased biomembrane transport such that the drug is more bioavailable from the GI tract, the rectum, the skin and the eye of the human body. A further object of this invention is to provide prodrug compounds which utilize hydrolytic enzymes to generate the parent amine-type drug from the prodrug or carbamate protecting group. It is a still further object of this invention to provide prodrugs of amines wherein the ester function is remote from the carbamate carbonyl and thus through enzymatic hydrolysis lead to the generation of carbamic acid which will undergo fast decarboxylation releasing the amine parent drug.

The (acyloxyalkoxy)carbonyl derivatives of the instant invention which are proposed as bioreversible prodrug moieties for primary and secondary amine functions in medicaments or drugs having these functions can be represented by the following formula:

Formula I wherein

RR'N represents the primary or secondary amine drug, pharmaceutical or medicament.

$R_1$ and $R_2$ can be different or the same radical and are selected from the group consisting of hydrogen or alkyl having from 1 to 6 carbon atoms such as methyl, ethyl, propyl, butyl or pentyl or substituted $C_{1-6}$ alkyl wherein the substituents are carboxyl or $C_{1-5}$ alkoxycarbonyl.

$R_3$ is alkyl having from 1 to 20 carbon atoms such as methyl, ethyl, hexadecyl and the like; alkenyl having from 2 to 20 carbon atoms such as butenyl, hexadecenyl, and the like; alkynyl having from 2 to 5 carbon atoms such as propargyl; aryl such as phenyl; aralkyl having from 6 to 8 carbon atoms such as benzyl; cycloalkyl having from 3 to 8 carbon atoms such as cyclohexyl or cyclopentyl; cycloalkenyl having from 3 to 10 carbon atoms such as cyclohexenyl; carboxyalkyl wherein the alkyl group has from 2 to 20 carbon atoms such as succinyl or glutaryl; carboxy cycloalkyl wherein the cycloalkyl group has from 5 to 20 carbon atoms such as carboxycyclohexyl, haloalkyl wherein the alkyl portion has from 2 to 20 carbons and halo is chloro, bromo, iodo or fluoro, such as chlorohexyl or chloropentyl; alkoxy carbonylalkyl wherein the alkyl carbonyl portion has from 2 to 10 carbon atoms and the alkoxy portion is $C_{1-5}$ such as carbethoxy hexyl; alkylsulfoxide wherein the alkyl group has from 2 to 20 carbon atoms such as ethyl sulfinyl propyl; carbamyl substituted alkyl or aralkyl having from 2 to 20 carbon atoms such as hexylcarboxamide; saturated or unsaturated mono- or polyheterocyclics having from 1 to 3 rings and having one or more of nitrogen, sulfur or oxygen atoms in the rings such as, for example, furyl, morpholinyl, oxazolidinyl, 1,2,5-thiazolyl and the like.

A preferred embodiment of my invention are the compounds of Formula I above wherein RR'N represent the primary or secondary amine function on a drug or medicament having said function thereon, $R_1$ and $R_2$ are hydrogen or loweralkyl having from 1 to 5 carbon atoms and are the same or different; and substituted $C_{1-5}$ alkyl wherein the substituents are carboxyl or $C_{1-5}$ alkoxy carbonyl; and $R_3$ is $C_{1-10}$ alkyl, $C_{2-10}$ alkenyl, $C_{2-5}$ alkynyl, $C_{3-8}$ cycloalkyl, $C_{5-15}$ carboxycycloalkyl, carboxy $C_{2-20}$ alkyl, or $C_{1-5}$ alkoxycarbonyl $C_{2-10}$ alkyl.

A still more preferred embodiment of my invention are those compounds of Formula I wherein RR'N represent the primary or secondary amine function on a drug or medicament.

having such functions thereon, $R_1$ and $R_2$ are the same or different and represent hydrogen or $C_{1-5}$ alkyl; $R_3$ is $C_{1-10}$ alkyl, carboxy, $C_{2-10}$ alkyl or $C_{1-5}$ alkoxycarbonyl $C_{2-10}$ alkyl.

As stated above, RR'N can represent any drug, pharmaceutical or medicament having a primary or secondary amine function thereon. Typical drugs, pharmaceuticals or medicaments which can be used and which have a primary or secondary amine function thereon are Timolol, thiabendazole, norfloxacin, dimethoxyphenethylamine, propranolol, atenolol and pindolol.

Some other drugs, pharmaceuticals or medicaments which can be used and which contain primary or secondary amine functions thereon are listed below. Those skilled in the art will realize that the list is not exclusive and the invention is applicable to other primary and secondary amino functional drugs as well.

(a) Those drugs, pharmaceuticals or medicaments similar to Timolol: acebutalol, albuterol, alprenolol, atenolol, bucindolol, bunolol, butopamine, butoxamine, carbuterol, cartelolol, colterol, deterenol, dexpropranolol, diacetolol, dobutamine, exaprolol, fenoterol, fenyripol, labotolol, levobunolol, metolol, metaproterenol, metoprolol, nadolol, oxprenolol, pamatolol, penbutalol, pindolol, pirbuterol, practolol, prenalterol, primidolol, prizidilol, procaterol, propranolol, quinterenol, rimiterol, ritodrine, sotolol, soterenol, sulfinolol, sulfonterol, suloctidil, tazolol, terbutaline, tiprenolol, tipropidil, tolamolol, etc.

(b) Structurally similar to thiabendazole: albendazole, albutoin, alinidine, alizapride, amiloride, aminorex, aprinocid, cambendazole, cimetidine, clonidine, cyclobendazole, etintidine, fenbendazole, fenmetazole, flubendazole, fludorex, lobendazole, mebendazole, metazoline, nocodazole, oxfendazole, oxibendazole, oxmetidine, parbendazole, ranitidine, tetrahydrazoline, tiamenidine, tinazoline, tiotidine, tolazoline, tramazoline, xylometazoline, etc.

(c) Structurally similar to dimethoxyphenethylamine: adrenelone, aletamine, amidephrine, amphetamine, aspartame, bamethan, betahistine, clorprenaline, chlortermine, dopamine, etryptamine, fenfluramine, norepinephrine, tocainide, etc.

Other drugs are acyclovir, enviroxime, etoprine, nifedipine, nimodipine, triamterene, vidarabine, methyldopa, epinephrine and those structurally similar to norfloxacin such as pipemidic acid, 1-ethyl-6-fluoro-1,4-dihydro-4-oxo-7-(1-piperazinyl)-1,8-naphthyridine-3-carboxylic acid and 1-cyclopropyl-6-fluoro-1,4-dihydro-4-oxo-7-(1-piperezinyl)-3-quinolinecarboxylic acid.

A general method for producing the prodrugs of Formula I of the present invention can be represented by the following chemical equation:

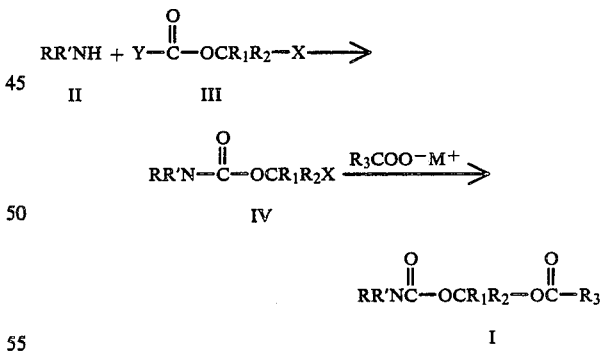

Thus the first step of the method for preparing compounds of Formula I consists of reacting a primary or secondary amine containing drug, pharmaceutical or medicidinal as described above of Formula II with an alkyl formate compound of Formula III wherein X is chloro, bromo or iodo or a similar group that undergoes ready neucleophilic displacement such as tosyl and Y represents a halogen or amine conjugate such as a pyridinium ion or a good leaving group (substituted phenoxy) such as p-nitrophenoxy, dinitrophenoxy, fluorophenoxy or difluorophenoxy and wherein $R_1$ and $R_2$ are independently hydrogen or alkyl having from 1 to 5 carbon atoms or substituted alkyl wherein the substituent is carboxyl or $C_{1-5}$ alkoxycarbonyl.

This first step of the reaction (Formula II to III) can be carried out in halogenated solvents such as chloroform or dichloromethane or in other nonprotic ether solvents such as tetrahydrofuran, dioxane, diethylether, dimethoxyethane, and the like or other solvents such as ethylacetate or acetonitrile. The reaction can be carried out at temperatures from $-78°$ C. to $50°$ C. but preferably is carried out at $0°$ C. to room temperature.

This first step of the reaction is also carried out in the presence of a base such as pyridine, triethylamine, 1,8-bis(dimethylamino), naphthalene, N-methylmorpholine and the like. The first step of the reaction gives a derivative shown as Formula IV in the above equation.

The second step of the reaction for preparing compounds of Formula I consists of displacing the X moiety with an acyl group and employs as a reactant for carrying them out an alkali or alkaline earth salt of a carboxylic acid or a metal salt of carboxylic acid. The metal ion M is selected from an alkali or alkaline earth metal such as sodium, potassium, magnesium, calcium, or can be a metal selected from silver, mercury, zinc and the like. This second step of the reaction can be carried out in a solvent which is inert to the reactant such as alcohol, water, dimethylformamide, hexamethylphosphoramide, acetonitrile or an organic acid such as acetic acid, propionic acid, and the like. This step of the reaction is carried out between ambient or room temperature to the boiling point of the particular solvent employed, but preferably between $25°$ C. to $150°$ C.

Both the first step of the reaction and the second step of the reaction are continued until the intermediate product IV and the final product I are respectively formed. The final product I can be isolated from the reaction mixture by methods known in the art such as by filtration or extraction into a solvent and concentration of the solvent to the particular compound of Formula I.

The prodrug compounds of Formula I of our invention can be used to treat any condition for which the parent amine or secondary amine containing drug, medicament or pharmaceutical is useful for. For example, if timolol is the parent drug of choice, the prodrug can be used for any condition or treatment for which timolol would be administered.

Thus, the prodrug compounds of Formula I may be administered orally, topically, parentally, by inhalation spray or rectally in dosage unit formulations containing conventional, non-toxic pharmaceutically acceptable carriers, adjuvants and vehicles.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation.

Formulations for oral use include tablets which contain the active ingredient in admixture with non-toxic pharmaceutically acceptable excipients. These excipients may be, for example, inert diluents, such as calcium carbonate, sodium chloride, lactose, calcium phosphate or sodium phosphate; granulating and disintegrating agents, for example, maize starch, or alginic acid; binding agents, for example, starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil.

Aqueous suspensions usually contain the active materials in admixture with appropriate excipients. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents which may be a naturally-occurring phosphatide, for example, lecithin; a condensation product of an alkylene oxide with a fatty acid, for example, polyoxyethylene stearate; a condensation product of ethylene oxide with a long chain aliphatic alcohol, for example, heptadecaethyleneoxycetanol; a condensation product of ethylene oxide with a partial ester derived from fatty acids and a hexitol such as polyoxyethylene sorbitol monooleate; or a condensation product of ethylene oxide with a partial ester derived from fatty acids and hexitol anhydrides, for example, polyoxyethylene sorbitan monooleate. The aqueous suspensions may also contain one or more preservatives, for example, ethyl, n-propyl, or p-hydroxybenzoate; one or more coloring agents; one or more flavoring agents; and one or more sweetening agents such as sucrose or saccharin.

Oily suspension may be formulated by suspending the active ingredient in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The pharmaceutical compositions of the invention may also be in the form of oil-in-water emulsions. The oily phase may be a vegetable oil, for example, olive oil or arachis oils, or a mineral oil, for example, liquid paraffin or mixtures of these. Suitable emulsifying agents may be naturally-occurring gums, for example, gum acacia or gum tragacanth; naturally-occurring phosphatides, for example, soybean lecithin; and esters including partial esters derived from fatty acids and hexitol anhydrides, for example, sorbitan mono-oleate, and condensation products of the said partial esters with ethylene oxide, for example, polyoxyethylene sorbitan monooleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may be a sterile injectable solution or suspension in a non-toxic parenterally-acceptable diluent or solvent. Among the acceptable vehicles and solvents that may be employed are water, 1,3-butanediol, Ringer's solution and isotonic sodium chloride solution. In addition, sterile fixed oils are conventionally employed as a solvent or suspending medium. For this purpose any bland fixed oil may be employed including synthetic mono- or diglycerides. Fatty acids such as oleic acid also find use in the preparation of injectibles.

The compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug, for example, cocoa butter and polyethylene glycols.

For topical use, creams, ointments, jellies, solutions, suspensions or the like containing the prodrugs are employed according to methods recognized in the art.

Naturally, therapeutic dosage range for the compounds of the instant invention will vary with the size and needs of the patient and the particular pain or disease symptom being treated. However, generally speaking, the following dosage guidelines will suffice. On an oral basis, the therapeutic dose required for a compound of the instant invention will generally, on a molecular basis, mimic that for the parent primary or secondary amine drug. On a topical basis, application of an 0.01% to 2.5% concentration of a compound of the instant invention (in a suitable topical carrier material) to the affected site should suffice.

From the foregoing description, one of ordinary skill in the art can easily ascertain the essential characteristics of the instant invention, and without departing from the spirit and scope thereof, can make various changes and/or modifications of the instant invention to adapt it to various usages and conditions. As such, these changes and/or modifications are properly, equitably and intended to be, within the full range of equivalence of the following claims.

The amount of active ingredient that may be combined with the carrier materials to produce a single dosage form will vary depending upon the host treated and the particular mode of administration. For example, a formulation intended for the oral administration of humans may contain from 5 mg to 5 gm of active agent compounded with an appropriate and convenient amount of carrier material which may vary from about 5 to about 95 percent of the total composition. Other dosage forms such as ophthalmic dosage forms contain less active ingredient such as for example from 0.1 mg to 5 mg. Dosage unit forms will generally contain between from about 0.1 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

As an illustration of this invention but not as a limitation thereof, the following examples embodying my invention are presented.

EXAMPLE 1

N-Chloromethoxycarbonyl-$\beta$-(3,4-dimethoxyphenyl)ethylamine

To an ice-cold solution of 0.1 g of dimethoxyphenethylamine in 25 ml of dichloromethane was added 1.07 g of 1,8-bis(dimethylamino)naphthalene (proton sponge®) followed by 0.7 g of chloromethyl chloroformate. After ½ hour, the cooling bath was removed and the reaction mixture was stirred at room temperature overnight. The reaction mixture was washed with water, 3N HCl and water. After drying over Na$_2$SO$_4$, the dichloromethane layer was evaporated to furnish 1.5 g of a light yellow mobile oil NMR (CDCl$_3$) $\delta$2.76 (2H, t, J=6 Hz, Ar CH$_2$), 3.45 m, 2H, NH CH$_2$), 2.83 (6H, s, OCH$_3$), 5.71 (2H, s, OCH$_2$Cl) and 6.71 (m, aromatic) IR (film) $\nu$ 3360, 2780, 1745, 1595, 1516, 1238, 1263 cm$^{-1}$.

EXAMPLE 2

N-(Acetoxymethoxy)carbonyl-$\beta$-(3,4-dimethoxyphenyl)ethylamine

The above chloromethylcarbamate (2.4 g) was dissolved in acetic acid (50 ml) and silver acetate (2.5 g) was added to it. It was heated in a water bath at 55°-60° with stirring for 3 hours. The reaction mixture was filtered through a pad of celite and the filtrate was evaporated in vacuum. The residue was dissolved in ether and filtered. The filtrate was evaporated to furnish 2.3 g of a pale yellow liquid which was pure by TLC. NMR (CDCl$_3$) $\delta$2.06 (3H, s, COMe), 2.76 (2H, t, J=6 Hz, Ar CH$_2$), 3.45 (2H, m, NHCH$_2$), 3.86 (6H, s, OMe), 5.16 (1H, t, broad, NH), 5.68 (2H, s, OCH$_2$O ) and 6.73 (3H, m, aromatic). IR (film) $\nu$3380, 2985, 1755, 1742, 1594, 1315, 1262, 1241, 1220 cm$^{-1}$.

EXAMPLE 3

1-Chloromethoxycarbonyl-2(4-thiazolyl)benzimidazole

To a suspension of 15.0 g of thiabendazole in 300 ml of chloroform, 6 g of pyridine was added and the suspension cooled in an ice bath. Chloromethyl chloroformate (10.6 g) was added to the reaction mixture dropwise during 10 minutes with stirring. A clear solution was formed which was kept stirred at room temperature for 16 hours. After washing the chloroform solution with water, it was dried over Na$_2$SO$_4$ and evaporated to a light yellow solid weighing 20.4 g. It was crystallized from EtOAc-CHCl$_3$. Obtained in two crops were 15.07 g of compound, m.p. 143°-144° NMR (CDCl$_3$) $\delta$5.9 (2H, s, OCH$_2$Cl), 7.2-8.2 (5H, m, aromatic), 8.93 (1H, d, J=3 Hz, aromatic). IR (KBr) $\nu$3095, 1780, 1460, 1374, 1340, 1194, 1140, 1078 cm$^{-1}$.

EXAMPLE 4

1-Iodomethoxycarbonyl-2(4-thiazolyl)benzimidazole

The above chloromethylcarbamate of thiabendazole (1 g) was dissolved in acetone (50 ml) and stirred at room temperature with sodium iodide (1 g) for 72 hours. The acetone was evaporated off. The residue taken in chloroform was washed with water, aqueous sodium bisulfite and water. The chloroform solution was evaporated to furnish 1.2 g of a light yellow solid which tended to decompose on attempting crystallize from EtOAc. NMR (CDCl$_3$) δ6.03 (2H, s, OCH$_2$I), 7.3–8.1 (5H, m, aromatic) and 8.96 (1H, d, J=3 Hz, aromatic).

EXAMPLE 5

1-(Acetoxymethoxy)carbonyl-2(4-thiazolyl)benzimidazole

Thiabendazole iodomethylcarbamate (1.2 g) was dissolved in acetic acid (50 ml) and stirred at room temperature with 0.6 g of silver acetate. After 2 hours, the reaction mixture was filtered and the filtrate was evaporated. The residue was taken in water and extracted with chloroform. The chloroform extract was washed with water and dried over Na$_2$SO$_4$. Evaporation of chloroform gave a thick oil (0.9 g) that slowly solidified. Crystallization from ethyl acetate-hexane gave 0.45 g pure acetoxymethylcarbamate in two crops. m.p. 104°–105°. NMR (CDCl$_3$) δ2.13 (3H, s, OAc), 5.91 (2H, s, OCH$_2$O), 7.3–8.2 (5H, m, aromatic) and 8.76 (1H, d, J=3 Hz, aromatic). IR (KBr) ν3096, 1778, 1752, 1458, 1360, 1337, 1230, 1210, 1194, 1050 cm$^{-1}$. m/e 317 (molecular ion).

Anal. Calc. for C$_{14}$H$_{11}$N$_3$O$_4$S: C, 52.98; H, 3.49; N, 13.24 and S, 10.1. Found: C, 52.76; H, 3.70; N, 13.06 and S, 10.16.

EXAMPLE 6

3-(3-N-Chloromethoxycarbonyl-tert-butylamino-2-hydroxypropoxy)-4-morpholino-1,2,5-thiadiazole Timolol (1.46 g) was dissolved in chloroform (50 ml) and 1,8-bis(dimethylamino)naphthalene (proton sponge ®, 1.00 g) was added to it. The solution was cooled in an ice bath and chloromethyl chloroformate (0.6 g) was added to the stirred solution during 5 minutes. The cooling bath was removed and the reaction mixture was stirred at room temperature overnight. It was washed with water, 3N hydrochloric acid and then with water. The chloroform solution was dried over Na$_2$SO$_4$ and evaporated to a thick oil weighing 1.72 g. TLC showed that the compound was practically pure.

NMR (CDCl$_3$) δ1.46 (9H, s, t-butyl), 2.96 (1H, s, OH, exchangeable with D$_2$O), 3.3–4.0 (10H, broad m, morpholino H and NCH$_2$), 4.20 (1H, m, CHOH), 4.5 (2H, m, OCH$_2$C) and 5.76 (2H, s, OCH$_2$Cl). IR (film) ν3400–3450, 1730, 1538, 1500, 1452, 1383, 1268, 1233, 1124, 1085 cm$^{-1}$.

EXAMPLE 7

3-[3-(N-Acetoxymethoxycarbonyl)-tert-butylamino-2-hydroxypropoxy]-4-morpholino-1,2,5-thiadiazole Chloromethylcarbamate of timolol from the above example, (1.10 g) was dissolved in acetic acid (50 ml) and silver acetate (1.2 g) was added to it. The reaction mixture was stirred at room temperature for 4½ hours. It was then filtered through celite and the filtrate was evaporated. The residue was taken in ether and filtered again. Evaporation of filtrate furnished a colorless thick oil weighing 1.2 g. It was contaminated with a minor impurity. A small sample was purified by preparative thin layer chromatography on silica gel. The chrometogram was developed with ethyl acetate-dichloromethane (2:8). The slower moving band corresponds to the required acetoxymethylcarbamate. NMR (CDCl$_3$) δ1.43 (9H, t-butyl), 2.08 (2H, s, CH$_3$CO), 3.6–3.8 (10H, broad m, morpholino H and NCH$_2$), 4.0–4.3 (1H, m, CHOH), 4.43 (2H, m, OCH$_2$C) and 5.73 (2H, s, OCH$_2$O). IR (film) ν3480, 1763, 1726, 1500, 1455, 1372, 1240 cm$^{-1}$. m/e 432 (molecular ion), 433 (M+1), 377, 287, 246, 174, etc.

EXAMPLE 8

1-Ethyl-6-fluoro-1,4-dihydro-4-oxo-7-(4-chloromethoxycarbonyl-1-piperazinyl)-3-quinolinecarboxylic acid Norfloxacin (6.4 g) was suspended in 300 ml of chloroform and 1.6 g of pyridine was added to it. The suspension was cooled in an ice bath and 2.85 g of chloromethyl chloroformate was added. A clear solution was formed in a few minutes. The cooling bath was removed and the reaction mixture was stirred for 16 hours at room temperature. The chloroform was evaporated off and the residue was suspended in water and stirred to break the solid. It was then filtered and washed with water. The product was dried. It weighed 4.9 g. A pure sample was obtained by crystallization from chloroform.

m.p. 207°–208° (DMSO-d$_6$) δ1.45 (3H, t, J=7 Hz, CH$_2$CH$_3$), 3.2–3.8 (8H, m, piperazine-H), 4.61 (2H, q, J=7 Hz, CH$_2$CH$_3$), 5.93 (2H, s, OCH$_2$Cl), 7.21 (1H, d, J=8 Hz, C$_8$—H), 7.90 (1H, d, J=14 Hz, C$_5$—H) and 8.93 (1H, s, C$_2$—H). IR (KBr) ν3460, 1726, 1482, 1450, 1243 cm$^{-1}$.

EXAMPLE 9

1-Ethyl-6-fluoro-1,4-dihydro-4-oxo-7-[4-(acetoxymethoxy carbonyl-1-piperazinyl]-3-quinolinecarboxylic acid Norfloxacin chloromethylcarbamate from Example 8 (5.6 g) was dissolved in dimethylformamide (50 ml) and heated with sodium acetate (3.5 g) for 20 hours at 100°–105°. The dimethylformamide was then evaporated off in vacuum. The residue was triturated with water and filtered. The filter cake was washed with water and dried. The light yellow solid weighed 5.2 g. It was crystallized from chloroform-hexane. Obtained in two crops was 3.7 g of a pale white solid, m.p. 248°–250°. NMR (CDCl$_3$) δ1.6 (3H, t, J=7 Hz, CH$_3$CH$_2$), 2.15 (3H, s, OAc), 3.2–3.9 (8H, m, piperazine-H), 4.38 (2H, q, J=7 Hz, CH$_3$CH$_2$), 5.82 (2H, s, OCH$_2$O), 6.865 (1H, d, J$_{H-F}$=7 Hz, 8-CH), 7.99 (1H, d, J$_{H-F}$=13 Hz, 5-CH), and 8.6 (1H, s, 2-CH). IR (KBr) ν3420–3480, 1762, 1726, 1635, 1486, 1256, 1222 cm$^{-1}$. m/e 435 (molecular ion), 391, 346, 320, 277, 275, 245, 233, 219, etc.

Anal. Calculated for C$_{20}$H$_{22}$O$_7$N$_3$F.H$_2$O: C, 52.96; H, 5.33 and N, 9.27. Found: C, 53.41; H, 5.31 and N, 9.75.

EXAMPLE 10

1-Ethyl-6-fluoro-1,4-dihydro-4-oxo-7-[(4-octanoyloxymethoxy carbonyl)-1-piperazinyl]-3-quinolinecarboxylic acid Norfloxacin chloromethylcarbamate from Example 8 (1.0 g) was dissolved in hexamethylphosphoric triamide (25 ml) and heated with sodium octanoate at 100° for 20 hours. The reaction mixture was diluted with water and extracted with chloroform. The chloroform extract was washed with water several times. It was dried over sodium sulfate and evaporated to a light brown solid. It was purified by crystallization from chloroform-hexane. NMR (CDCl$_3$) δ0.9 (3H, unresolved t, C$\underline{H}_3$ alkyl), 1.1–2.0 (15H, unresolved m, CH$_2$ alkyl and NC$\underline{H_2CH_3}$), 2.48 (2H, m, COC$\underline{H}_2$), 3.2–3.9 (8H, m, piperazine $\underline{H}$), 4.36 (2H, q, J=7 $\underline{Hz}$, CH$_3$C$\underline{H}_2$N), 5.80 (2H, s, OC$\underline{H_2}$O), 6.85 (1H, d, J$_{H-F}$=7 Hz, 8-C$\underline{H}$), 7.98 (1H, d, J$_{H-F}$=12 Hz, 5-C$\underline{H}$) and 8.6 (1H, s, 2-C$\underline{H}$). IR (KBr) ν3460, 1758, 1726, 1634 cm$^{-1}$.

EXAMPLE 11

N-(1-Chloroethoxycarbonyl)-β-(3,4-dimethoxyphenyl)ethylamine

To a solution of 1.8 g of 3,4-dimethoxyphenethylamine in 50 ml of chloroform 2.2 g of proton sponge ® was added. The reaction mixture was cooled in an ice bath. To the ice-cold solution was added with stirring 1.4 g of 1-chloroethyl chloroformate. The cooling bath was removed and the reaction mixture was kept stirred at room temperature for 72 hours. It was then washed with water, 3N HCl and water. After drying over sodium sulfate, the chloroform solution was evaporated to a thick oil weighing 2.1 g. NMR (CDCl$_3$) δ1.75 (3H, d, J=7 Hz, C$\underline{H_3CH}$), 2.78 (2H, t, J=6 Hz, ArC$\underline{H}_2$), 3.4 (2H, broad t, NHC$\underline{H}_2$), 3.9 (6H, s, OMe), 4.9 (1$\underline{H}$, broad NH) and 6.4–6.85 (CHCl and aromatic). IR (film) ν3350, 1722, 1512, 1260, 1240, 1138 cm$^{-1}$.

EXAMPLE 12

N-(1-Acetoxyethoxycarbonyl)-β-(3,4-dimethoxyphenyl)ethylamine

The chloroethyl carbamate from Example 11 (0.25 g) was dissolved in acetic acid (25 ml) and mercuric acetate (1.0 g) was added to it. The reaction mixture was stirred at room temperature for 3 hours. It was filtered and the filtrate was evaporated in vacuum at room temperature. The residue was dissolved in ether and filtered. Evaporation of ether gave a thick oil weighing 0.21 g as a practically pure compound. An analytical sample was prepared by filtering through silica gel in chloroform. NMR (CDCl$_3$) δ1.45 (3H, d, J=7 Hz, C$\underline{H_3CH}$), 2.06 (3H, s, OA$\underline{c}$), 2.76 (2H, t, J=7 Hz), ArC$\underline{H}_2$), 3.38 (2H, t, J=7 Hz, NHC$\underline{H}_2$), 3.9 (6H, s, OM$\underline{e}$), 5.06 (1H, broad t, N$\underline{H}$) and 6.6–7.0 (4H, CHCH$_3$ and aromatic). IR (film) ν3345, 1742, 1723, 1515, 1262, 1238 cm$^{-1}$. m/e 311 (M+), 207, 164, 151, etc.

Anal. calculated for C$_{15}$H$_{21}$NO$_6$: C, 57.86; H, 6.80; N, 4.50. Found: C, 57.67; H, 6.80; N, 4.60.

EXAMPLE 13

1-Ethyl-6-fluoro-1,4-dihydro-4-oxo-7-[4-(1-chloroethoxy carbonyl)-1-piperazinyl]-3-quinoline carboxylic acid Norfloxacin (6.4 g) was suspended in 300 ml of chloroform and 4.3 g of proton sponge ® was added to it. The suspension was cooled in an ice bath and 4.0 g of 1-chloroethyl chloroformate was added. A clear solution resulted in half an hour. The reaction mixture was stirred at room temperature for 14 hours. The reaction mixture was concentrated in vacuum to about 150 ml. The crystals formed were filtered and washed with chloroform. The pure product weighed 5.3 g.

EXAMPLE 14

1-Ethyl-6-fluoro-1,4-dihydro-4-oxo-7-[4-(11-acetoxyethoxycarbonyl)-1-piperazinyl]-3-quinolinecarboxylic acid The chloroethyl carbamate from Example 13 (3.0 g) was suspended in acetic acid (150 ml) and mercuric acetate (3.0 g) was added to it. The reaction mixture was stirred at room temperature for 96 hours. The acetic acid was evaporated off in vacuum at room temperature. The residue was taken in chloroform and washed with water (×3) and dried over sodium sulfate. Evaporation of chloroform gave a solid weighing 3.2 g as a white crystalline solid. It was crystallized from dichloromethane-ethyl acetate. m.p. 215°–217°. NMR (CDCl$_3$) δ1.5 (3H, d, J=7 Hz, C$\underline{H_3CH}$), 1.55 (3H, t, C$\underline{H_3CH_2}$), 2.06 (3H, s, OA$\underline{c}$), 3.2–3.9 (8H, piperazine $\underline{H}$), 4.33 (2H, q, CH$_3$C$\underline{H}_2$), 6.66–7.0 (2H, overlapping 8-C$\underline{H}$ and CH$_3$C$\underline{H}$), 7.9 (1H, d, J$_{H-F}$=12 Hz, 5-C$\underline{H}$) and 8.6 (1H, s, 2-C$\underline{H}$). IR (KBr, reflectance) ν1753, 1715, 1627 cm$^{-1}$. m/e 449 (M+).

EXAMPLE 15

1-[N-(1-Chloroethoxycarbonyl)isopropylamino]-3-(1-naphthyloxy)-2-propanol

A suspension of propanolol hydrochloride (3.0 g) in chloroform (100 ml) was mixed with proton sponge ® (4.3 g) and cooled in an ice bath. 1-Chloroethyl chloroformate (1.5 g) was added dropwise to the reaction mixture. The suspension dissolved in about 5 minutes. The cooling bath was removed and the reaction mixture was stirred at room temperature for 1.5 hours. The chloroform solution was washed with water, 3N HCl and water successively. The organic layer was dried over Na$_2$SO$_4$ and evaporated to a thick oil weighing 3.6 g. NMR (CDCl$_3$) δ1.25 (6H, d, J=7 Hz, CH(M$\underline{e}$)$_2$), 1.8 (3H, d, J=7 Hz, CH$_3$C$\underline{H}$), 3.3=3.6 (3H, m, ArOCH$_2$ and C$\underline{H}$(Me)$_2$), 4.0–4.6 (3H, m, NCH$_2$ and C$\underline{HOH}$), 6.61 (1H, q, J=7 Hz, CH$_3$C$\underline{H}$) and 6.7–8.4 (7H, m, aromatic). IR (film) ν3450, 1715, 1583, 1270, 1248, 1108 cm$^{-1}$.

EXAMPLE 16

1-[N-(1-Acetoxyethoxycarbonyl)isopropylamino]-3-(1-naphthloxy)-2-propanol

The chloroethyl carbamate from Example 15 (3.6 g) was dissolved in acetic acid (60 ml) and mercuric acetate (3.2 g) was added to it. The reaction mixture was stirred at room temperature for 72 hours. The acetic acid was evaporated off in vacuum. The residue was taken in ether and washed successively with water, 3N HCl and water. The ether layer was dried over Na$_2$SO$_4$ and evaporated to a thick oil. A small amount was purified by preparative thin layer chromatography from a small amount of a very polar impurity. NMR (CDCl$_3$) δ1.20 and 1.24 (6H, 2 doublets, J=7 Hz, CH(C$\underline{H_3}$)$_2$), 1.49 (3H, d, J=7 Hz, C$\underline{H_3CH}$), 2.05 (3H, s, OAc), 3.51 (2H, d, J=7 Hz, ArOC$\underline{H}_2$), 3.9–4.5 (4H, C$\underline{H}$(OH)CH$_2$ and NC$\underline{H}$(CH$_3$)$_2$), 6.80 (1H, q, J=7 Hz, C$\underline{H_3CH}$) and 6.6–8.3 (7H, aromatic). IR (film) ν3470, 1745, 1705, 1585, 1270, 1238, 1105, 1076 cm$^{-1}$. m/e 389 (M+), 286, 202, 160, 144, etc.

What is claimed is:

1. A compound of the formula:

wherein
RR'N represents an amino substituted primary or secondary amine pharmaceutical;
$R_1$ and $R_2$ are selected from the group consisting of hydrogen, and substituted $C_{1-6}$alkyl or alkyl wherein the substituents are carboxy or $C_{1-5}$alkoxy carbonyl
$R_3$ is selected from the group consisting of
$C_{1-20}$ alkyl
$C_{2-20}$ alkenyl
$C_{2-5}$ alkynyl
aryl
$C_{6-8}$ aralkyl
$C_{3-8}$ cycloalkyl
$C_{3-10}$ cycloalkenyl
carboxy $C_{2-20}$ alkyl
carboxy $C_{5-20}$ cycloalkyl
halo $(C_{2-20})$ alkyl.

2. A compound of claim 1 wherein the RR'N group is an amino substituted primary or secondary amine pharmaceutical;
$R_1$ and $R_2$ are the same or different and are selected from the group consisting of
hydrogen and
$C_{1-5}$ alkyl and
$R_3$ is selected from the group consisting of
$C_{1-10}$ alkyl
carboxy $C_{2-10}$ alkyl and
$C_{1-5}$ alkoxy carboxyl $C_{2-10}$ alkyl.

3. A compound of claim 1 wherein the RR'N primary or secondary amine pharmaceutical is selected from the group consisting of timolol, thiabendazole, norfloxacin, dimethoxyphenethylamine, propranolol, atenolol, pindolol, methyldopa, epinephrine, dopamine, metoprolol, cartelolol, pipemidic acid, 1-ethyl-6-fluoro-1,4-dihydro-4-oxo-7-(1-piperazinyl)-1,8-naphthyridine-3-carboxylic acid and 1-cyclopropyl-6-fluoro-1,4-dihydro-4-oxo-7-(1-piperezinyl)-3-quinolinecarboxylic acid.

4. A compound of claim 1 which is 1-(Acetoxymethoxy)carbonyl-2-(4-thiazolyl)benzimidazole.

5. A compound of claim 1 which is 3-[3-(N-acetoxymethoxycarbonyl)tert-butylamino-2-hydroxypropoxy]-4-morpholino-1,2,5-thiadiazole.

6. A compound of claim 1 which is 1-ethyl-6-fluoro-1,4-dihydro-4-oxo-7-[4-(acetoxymethoxycarbonyl-1-piperazinyl]-3-quinolinecarboxylic acid.

7. A compound of claim 1 which is 1-ethyl-6-fluoro-1,4-dihydro-4-oxo-7-[(4-octanoyloxymethoxycarbonyl)1-piperazinyl]-3-quinolinecarboxylic acid.

8. A compound of claim 1 which is 1-ethyl-6-fluoro-1,4-dihydro-4-oxo-7-[4-(1-acetoxyethoxycarbonyl)-1-piperazinyl]-3-quinolinecarboxylic acid.

9. A compound of claim 1 which is 1-[N-(1-acetoxyethoxycarbonyl)isopropylamino]-3-(1-naphthloxy)-2-propanol.

10. A pharmaceutical composition comprising a compound of claim 1 and a suitable pharmaceutical carrier.

11. A pharmaceutical composition comprising a compound of claim 2 and a suitable pharmaceutical carrier.

12. A pharmaceutical composition comprising a compound of claim 3 and a suitable pharmaceutical carrier.

13. A method for alleviating pain or disease symptoms in a warm-blooded animal exhibiting pain or disease symptoms which comprises administering thereto an anti-pain or anti-disease symptom effective amount of a compound of claim 1.

14. A method for alleviating pain or disease symptoms in or on a warm-blooded animal exhibiting pain or disease symptoms which comprises administering thereto an anti-pain or anti-disease symptom effective amount of a compound of claim 2.

15. A method for alleviating pain or disease symptoms in or on a warm-blooded animal exhibiting pain or disease symptoms which comprises administering thereto an anti-pain or anti-disease symptom effective amount of a compound of claim 3.

* * * * *